US00PP28370P2

(12) United States Plant Patent
Rijsewijk

(10) Patent No.: US PP28,370 P2
(45) Date of Patent: Sep. 12, 2017

(54) ***PLATANUS* TREE NAMED 'WOODSIDE COLUMN'**

(50) Latin Name: *Platanus×hispanica*
Varietal Denomination: Woodside Column

(71) Applicant: Hans van Rijsewijk, Oisterwijk (NL)

(72) Inventor: Hans van Rijsewijk, Oisterwijk (NL)

(73) Assignee: BOOMKWEKERIJ GEBR. VAN DEN BERK BV, Sint-Oedenrode (NL)

( * ) Notice: Subject to any disclaimer, the term of this patent is extended or adjusted under 35 U.S.C. 154(b) by 24 days.

(21) Appl. No.: 14/998,565

(22) Filed: Jan. 19, 2016

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Keith Robinson
(74) *Attorney, Agent, or Firm* — Penny J. Aguirre

(57) ABSTRACT

A new cultivar of *Platanus*, 'Woodside Column', that is characterized by its narrow upright plant habit, its ease of propagation by softwood stem cuttings, its ease of transplanting with good re-growth, and its moderate growth habit.

2 Drawing Sheets

Botanical classification: *Platanus×hispanica.*
Variety denomination: 'Woodside Column'.

CROSS REFERENCE TO A RELATED APPLICATION

This application is related to a European plant breeders' rights application filed on Apr. 23, 2012, application No. 2012/0873. There have been no offers for sale anywhere in the world prior to the filing of this Application and no accessibility to one of ordinary skill in the art could have been derived from printed plant breeder's rights documents.

BACKGROUND OF THE INVENTION

The present invention relates to a new and distinct cultivar of *Platanus×hispanica* (syn. *Platanus×acerifolia*), and will be referred to hereafter by its cultivar name, 'Woodside Column'. 'Woodside Column' is a deciduous tree grown for use as a landscape plant.

The Inventors selected the new cultivar, 'Woodside Column', as a chance seedling in Oisterwijk, the Netherlands in the September of 2001. The seedbed had been planted with seeds collected from unnamed and unpatented open pollinated plants of *Platanus×hispanica.*

Asexual reproduction of the new cultivar was first accomplished by softwood stem cuttings under the direction of the Inventor in Sint-Oedenrode, Netherlands in December of 2002. Asexual propagation of 'Woodside Column' by softwood stem cuttings has shown that the unique features of the new cultivar are stable and are reproduced true to type in successive generations.

SUMMARY OF THE INVENTION

The following traits have been repeatedly observed and represent the characteristics of the new cultivar. These attributes in combination distinguish 'Woodside Column' as a new and unique cultivar of *Platanus.*

1. 'Woodside Column' exhibits a narrow upright plant habit.
2. 'Woodside Column' is readily propagated by softwood stem cuttings.
3. 'Woodside Column' is readily transplanted (good re-growth).
4. 'Woodside Column' has a moderate growth habit.

Typical plants of *Platanus×hispanica* differ from 'Woodside Column' in having a broadly ovate to near rounded crown shaped habit and in being more difficult to propagate from softwood stem stem cuttings. 'Woodside Column' can also be compared to *Platanus×hispanica* cultivars 'Tremonia' (not patented) and 'Mr. X' (not patented). 'Tremonia' and 'Mr. X' are both similar to 'Woodside Column' in having an upright plant shape. 'Tremonia' differs from 'Woodside Column' in having a faster growth rate, in being more difficult to propagate from stem cuttings and in being less easy to transplant. 'Mr. X' differs from 'Woodside Column' in having young foliage that is purplish red in color (rather than yellow-green as observed for 'Woodside Column'), and in having leaf buds that are red in color (rather than yellow-green as observed for 'Woodside Column').

BRIEF DESCRIPTION OF THE DRAWINGS

The accompanying colored photographs illustrate the overall appearance and distinct characteristics of the new *Platanus*, 'Woodside Column'. The photographs were taken of 5 year-old plants of 'Woodside Column' as field grown in Sint-Oedenrode, Netherlands.

Figure 1:
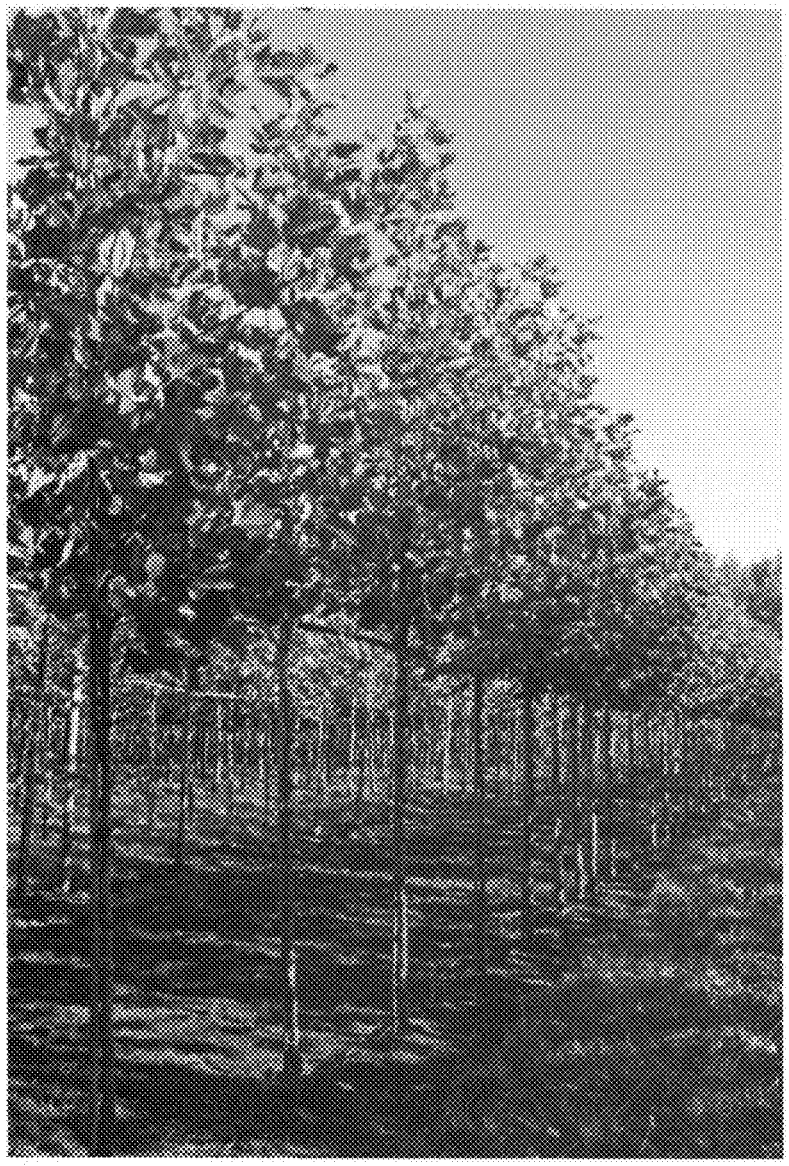
FIG. 1 provides an overall view of the plant habit of plants of 'Woodside Column'.
Figure 2:
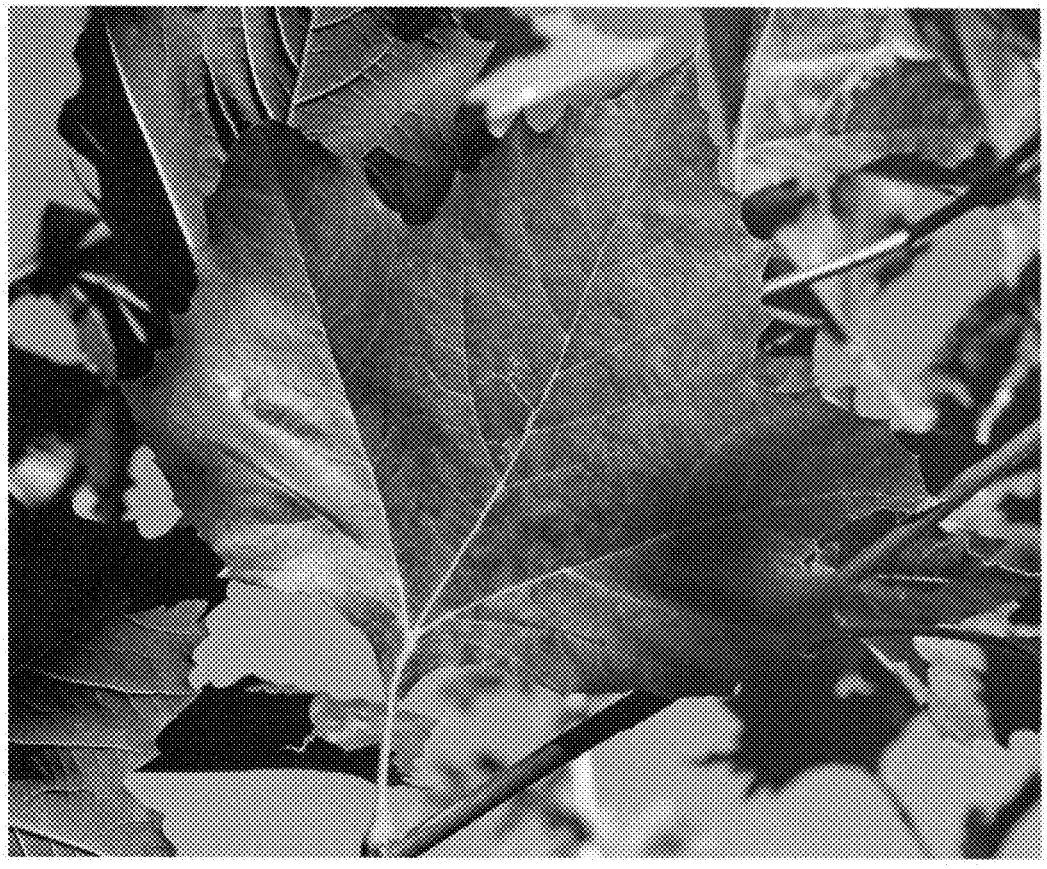

The photograph in FIG. 2 provides a close-up view of a leaf of 'Woodside Column' in fall.

The colors in the photographs are as close as possible with the photographic and printing technology utilized and the color values cited in the Detailed Botanical Description accurately describe the colors of the new *Platanus.*

DETAILED BOTANICAL DESCRIPTION

The following is a detailed description of a five-year old plant of the new cultivar as field grown in Sint-Oedenrode, Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type*.—Deciduous tree.

*Plant habit*.—Upright with narrow ovate crown.

*Height and spread*.—An average of 4 m in height and 1.5 m in spread, mature height in the landscape is an average of 25 m in height and 10 m in width.

*Cold hardiness*.—At least to U.S.D.A. Zone 6.

*Diseases and pests*.—No susceptibility or resistance to diseases or pests was observed.

*Root description*.—Fibrous, freely branched.

*Propagation*.—Softwood stem cuttings.

*Root development*.—About 3 months to produce a young rooted plant from a cutting initiated in spring.

*Growth rate*.—Moderately vigorous, slow growing.

Branch description:

*Shape*.—Elliptic.

*Branch color*.—Young; 144A, later fading to 152A, mature branches and main stem; N199A.

*Branch size*.—Lateral branches; an average of 104 cm in length and 7.5 mm in diameter, main trunk; an average of 6 cm in width measured 12 cm from soil line.

*Branch surface*.—Glabrous and glossy with young stems densely covered with small stellate hairs, an average of 0.1 mm in length and 160D in color, all stems moderately to densely covered with lenticels, an average of 0.3 mm in length and 199C in color, mature bark is smooth and becomes exfoliating as a mature tree.

*Internode length*.—Average of 9.6 cm.

*Branch aspect*.—Lateral branches held at an angle of 45° to main stem.

*Branch strength*.—Very strong.

*Branching*.—Freely branching, an average of 35 lateral branches, pinching is not required, but will improve branching.

Foliage description:

*Leaf shape*.—Palmately lobed.

*Leaf division*.—Simple.

*Leaf quantity*.—An average of 11 leaves per lateral branch.

*Leaf base*.—Broadly acuminate.

*Leaf apex*.—Broadly acuminate.

*Leaf fragrance*.—None.

*Leaf venation*.—Laciniate, N144A on upper surface and 151D on lower surface.

*Leaf margins*.—Coarsely serrate-dentate.

*Leaf arrangement*.—Alternate.

*Leaf aspect*.—Held straight from petioles.

*Leaf attachment*.—Petiolate.

*Leaf surface*.—Upper surface; moderately glossy, lower side slightly glossy and densely covered with stellate hairs on the main, secondary and tertiary veins, average hair length is 0.1 mm and 160D in color.

*Leaf size*.—Up to 19.2 cm in length and 20.1 cm width.

*Leaf color*.—Young upper surface; 146B to 146C, young lower surface; 146C, mature upper surface; between NN137A and 147A, mature lower surface; 146B.

*Petioles*.—Average of 3.6 cm in length and 2.5 mm in width, held at about a 45° angle from branch, color of upper and lower surface N144A.

*Leaf buds*.—Surface completely covered by the proximal part of the petiole, ovate in shape, average of 8 mm in length and 6 mm in diameter, 143B to 143C in color.

*Stipules*.—None.

Inflorescence description: No flowers have been observed to date.

It is claimed:

1. A new and distinct cultivar of *Platanus* tree named 'Woodside Column' as herein illustrated and described.

* * * * *